United States Patent
Pawlowicz et al.

(10) Patent No.: US 8,791,436 B1
(45) Date of Patent: Jul. 29, 2014

(54) CIRCUIT TRACING USING A FOCUSED ION BEAM

(71) Applicants: Chris Pawlowicz, Ottawa (CA);
Alexander Sorkin, Nepean (CA);
Michael W. Phaneuf, Ottawa (CA);
Alexander Krechmer, Ottawa (CA);
Ken G. Lagarec, Ottawa (CA)

(72) Inventors: Chris Pawlowicz, Ottawa (CA);
Alexander Sorkin, Nepean (CA);
Michael W. Phaneuf, Ottawa (CA);
Alexander Krechmer, Ottawa (CA);
Ken G. Lagarec, Ottawa (CA)

( * ) Notice: Subject to any disclaimer, the term of this patent is extended or adjusted under 35 U.S.C. 154(b) by 0 days.

(21) Appl. No.: 13/869,749

(22) Filed: Apr. 24, 2013

(51) Int. Cl.
*G21G 5/00* (2006.01)
*H01J 37/26* (2006.01)

(52) U.S. Cl.
CPC ............. *H01J 37/26* (2013.01); *H01J 2237/28* (2013.01); *H01J 2237/2806* (2013.01)
USPC ..... 250/492.3; 250/306; 250/307; 250/492.1; 250/492.2

(58) Field of Classification Search
CPC ............ H01J 2237/28; H01J 2237/244; H01J 2237/2516; H01J 2237/2806; H01J 37/26; G01N 23/2251; G01N 27/60
USPC .......... 250/306, 307, 309, 311, 492.1, 492.2, 250/492.21, 492.3
See application file for complete search history.

(56) References Cited

U.S. PATENT DOCUMENTS

2008/0237487 A1* 10/2008 Pinto et al. ................. 250/492.1
2010/0038555 A1* 2/2010 Tsao ............................ 250/397

* cited by examiner

*Primary Examiner* — Nicole Ippolito
*Assistant Examiner* — Hanway Chang
(74) *Attorney, Agent, or Firm* — Moore & Van Allen PLLC

(57) ABSTRACT

Methods and systems for tracing circuitry on integrated circuits using focused ion beam based imaging techniques. A first component or node on an integrated circuit is coupled to a second component or node on the same integrated circuit. After an external bias is applied to the first component or node, a focused ion beam is applied to the integrated circuit and an image is taken using an electron detector. The features or components on the integrated circuit which are coupled to the second component or node will show up in high contrast on the resulting image. The method may also involve applying a bias to a node or component and then using focused ion beam imaging techniques (through an electron detector) to arrive at an image of the integrated circuit. Components coupled to the node will appear in high contrast in the resulting image.

15 Claims, 5 Drawing Sheets

US 8,791,436 B1

CIRCUIT TRACING USING A FOCUSED ION BEAM

TECHNICAL FIELD

The present invention relates to circuit tracing. More specifically, the present invention relates to methods and systems for use in tracing circuit connections on an integrated circuit using a focused ion beam to capture an image of the circuit.

BACKGROUND OF THE INVENTION

The technological revolution of the late 20th and early 21st century has put a premium on competitive corporate intelligence. Companies, especially those involved in high tech, seek to determine what their competitors are putting in their latest products. To this end, integrated circuits, especially high value, cutting edge microchips, are constantly being reverse engineered, analyzed, and dissected to determine what are their internal structures and interconnections.

Currently, the dissection and analysis of integrated circuits involves a painstaking, laborious process. Each layer in a multi-layer microchip is carefully exposed and imaged/photographed. A mosaic of the images is then created and the traces are then laboriously traced to determine which feature is interconnected with which component. As can be imagined, this resource-intensive process can lead to mistakes as features and areas which may not be of interest may need to be imaged and analyzed, simply to ensure that the features of interest are covered.

There is therefore a need for systems, methods, and devices which can reduce the effort required to trace circuits and interconnects on integrated circuits.

SUMMARY OF INVENTION

The present invention provides methods and systems for tracing circuitry on integrated circuits using focused ion beam based imaging techniques. A first component or node on an integrated circuit is coupled to a second component or node on the same integrated circuit. An external bias is then applied to the first component or node. A focused ion beam is applied to the integrated circuit and an image is taken using an electron detector. The features or components on the integrated circuit which are coupled to the second component or node will show up in high contrast on the resulting image. The method can be used in an iterative process to identify which components are coupled to which features on the integrated circuit. The method may also involve applying a bias to a node or component and then using focused ion beam imaging techniques (through an electron detector) to arrive at an image of the integrated circuit. Other components or nodes coupled to the node or component to which the bias was applied will appear in high contrast on the resulting image.

In a first aspect, the present invention provides a method for imaging circuitry on an integrated circuit, the method comprising:
a) coupling a first part of said integrated circuit with a second part of said integrated circuit;
b) applying a bias voltage to said first part;
c) exposing said integrated circuit to a focused ion beam; and
d) gathering an image of said integrated circuit using an electron detector;
wherein said first part and said second part are not coupled through said integrated circuit; and
wherein said image gathered in step d) has at least one portion in high contrast compared to a rest of said image, said at least one portion being a portion of said integrated circuit which is coupled to said second part of said integrated circuit.

In a second aspect, the present invention provides a method for tracing interconnections in an integrated circuit, the method comprising:
a) removing layers of said integrated circuit to expose components of said integrated circuit;
b) coupling a first node of said integrated circuit to a second node of said integrated circuit;
c) applying an external bias voltage to said first node;
d) capturing an image of at least a portion of said integrated circuit using a focused ion beam and an electron detector;
e) determining which components of said integrated circuit are illustrated in high contrast in said image;
wherein, prior to step b), said first node and second node are not coupled to one another through said integrated circuit.

In a third aspect, the present invention provides a method for imaging circuitry on an integrated circuit, the method comprising:
a) applying an external electrical bias on to a first portion of said integrated circuit;
b) exposing said integrated circuit to a focused ion beam;
c) gathering an image of said integrated circuit;
wherein said image gathered in step c) shows a second portion of said integrated circuit which is in high contrast compared to a rest of said image, said first and second portions being interconnected through a common path in said integrated circuit.

BRIEF DESCRIPTION OF THE DRAWINGS

The embodiments of the present invention will now be described by reference to the following figures, in which identical reference numerals in different figures indicate identical elements and in which.

DETAILED DESCRIPTION OF THE INVENTION

Focused Ion Beam (FIB) systems are well established in the semiconductor industry and come in a variety of configurations for a number of different uses. In FIB systems, a focused beam is generated and the beam is accelerated down a column. The beam is then manipulated by applying electromagnetic energy through a system of coils (and electrostatic lenses), and the resulting beam emerges in a vacuum chamber and strikes a sample/target. For FIB, the beam consists of ions as ion beams have much more kinetic energy than electron beams. By striking a sample with high power, material can be milled away and removed. By adding background gas and striking the sample with lower energy, new material can be deposited. By manipulating the beam and adding a gas, one can deposit and remove material in a precise and controlled manner. Standard gases which may be used include xenon difluoride, tetramethylcyclotetrasiloxane (TMCTS), platinum, tungsten, and other well-known gases.

After the ion beam strikes a sample, ions, atoms and electrons are emitted (mostly 'secondary electrons'). These electrons can be used to create an image—an image can be obtained by using an electron detector and synchronizing the collected signal with the ion beam scanning. Depending on the sample's materials and other factors, more or less electrons might be emitted. The image can therefore be used to identify regions of the sample with different characteristics. As an example, metal circuitry will emit a different number of electrons than dielectric areas and this causes metal circuitry to appear different than dielectric areas in the image.

Figure 1:
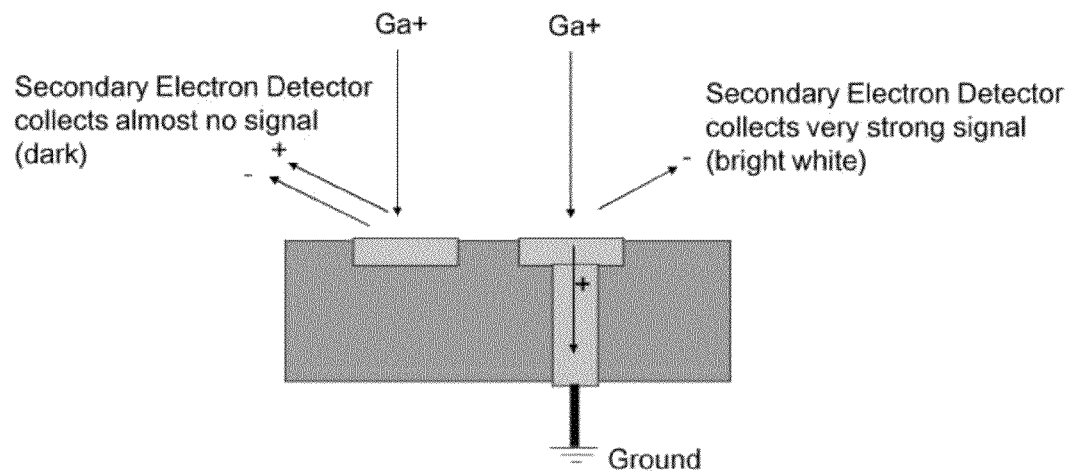
FIGS. 1 and 2 are schematic diagrams provided to explain focused ion beam (FIB) technology.

Referring to FIG. 1, a schematic view explaining focused ion beam technology is illustrated. As can be seen in FIG. 1, a focused ion beam (from a gallium ion source) is applied to a sample. The ion beam causes electrons to be emitted by the sample. These electrons are detected by a secondary electron detector. From the emitted electrons, an image of the sample can be constructed. As can also be seen in FIG. 1, by grounding one of the features of the sample and thereby rerouting positive particles, a brighter image can be obtained for the grounded feature. This is because the secondary electron detector receives a higher concentration of electrons compared to the ungrounded feature.

A well known phenomenon occurs when an ion beam strikes an area of semiconductor with embedded dopant material. Since N-doped silicon behaves differently from P-doped silicon when struck by an ion beam, the resulting image shows contrast differences between the materials. Materials other than semiconductors also show this behaviour, known as voltage contrast, in various degrees.

Figure 2:
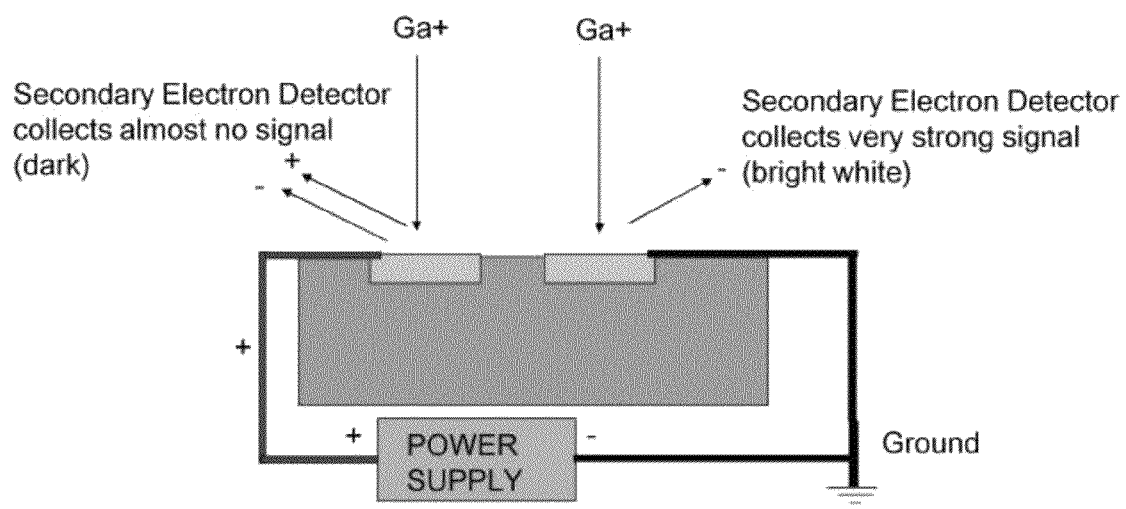

By way of explanation, FIG. 2 is provided. In this Figure, two features on an integrated circuit (IC) are coupled by means of an electrical circuit. When a focused ion beam is applied to the features, the feature on the IC which is coupled to ground produces a brighter image. Again, this is because the secondary electron detector receives a higher concentration of electrons from the grounded feature as compared to the ungrounded feature.

Figure 3:
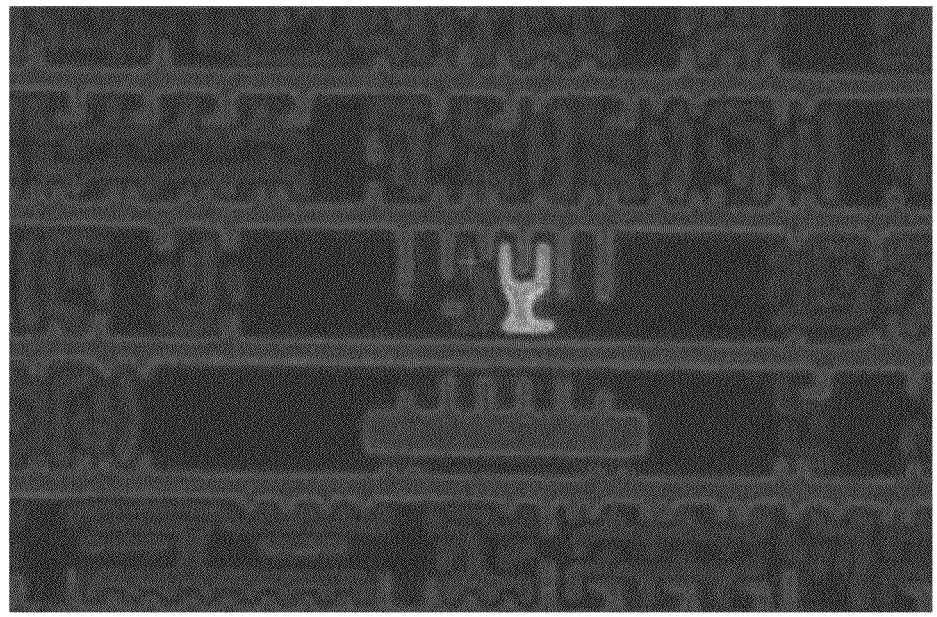
FIG. 3 is an image derived from FIB illustrating a feature of an IC in high contrast.

Extending the concept explained by FIG. 2, a focused ion beam can be used to strike a sample which has a mixture of dielectric material and metal interconnect (e.g. a delayered IC die). By making external connections to specific areas of circuitry and applying a bias voltage to those areas, the amount of electrons generated when these areas are struck by an ion beam can be made to vary greatly. Using this technique, specific areas of the integrated circuit can be made to show much higher brightness (i.e. higher contrast) in the resulting image as compared to other areas when plotting the secondary electron yield. One example of this is shown in FIG. 3 where an IC feature/component has been biased and an FIB has been applied. As can be seen, the feature to which a bias has been applied is in high contrast to the rest of the IC.

The high brightness (or high contrast) area can be extended by using normal circuit-edit FIB manipulation. By depositing dielectric material, milling access holes, and depositing metal interconnect, the biased area can be connected to a new area or a new component or node of the IC. Any areas, components, or nodes coupled to the biased area will, when struck by a focused ion beam, similarly appear in high contrast in the resulting image derived from the secondary electron detector output. This can be used to determine which features, nodes, or components on an IC are connected to which areas, features, nodes, or components.

Figure 3A:
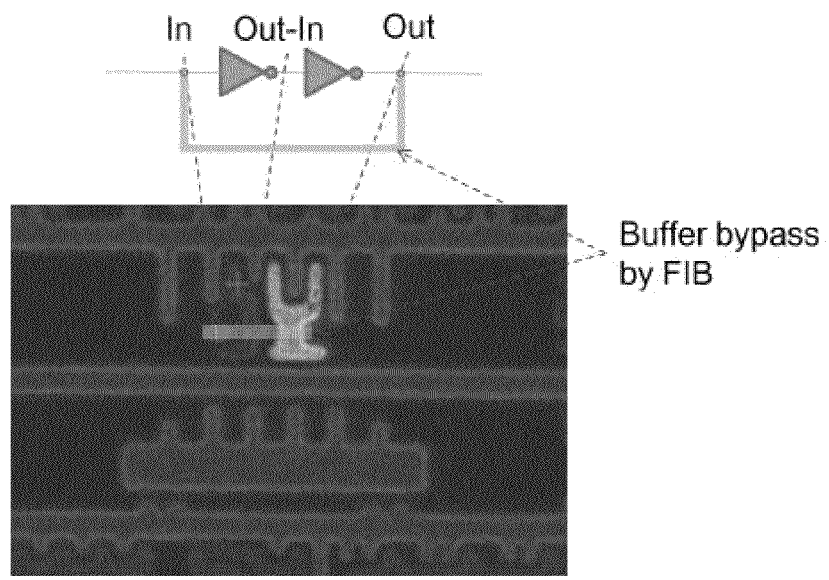
FIG. 3A is a schematic diagram with an image from FIB showing the coupling between two features on an IC.

Referring to FIGS. 3A-6, the steps in the coupling between a known feature and an unknown area or feature in the IC is illustrated. FIG. 3A shows, in a schematic diagram, the desired end result for shorting two features on the IC. As can be seen, a known feature (the buffer feature in high contrast) is to be shorted with an adjacent feature, also a buffer. The yellow block between the highlighted buffer component and its adjacent buffer represents a short that couples these buffers to one another in FIG. 3A.

Figure 4:
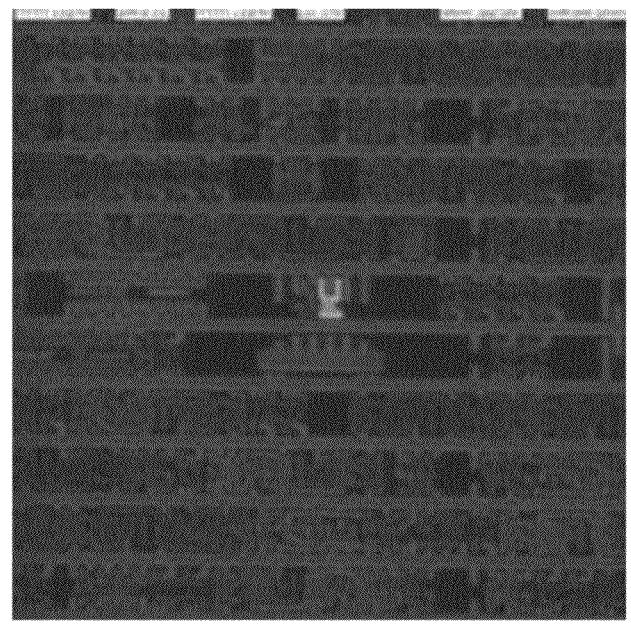
FIG. 4 is an image of a feature in high contrast using FIB.
Figure 5:
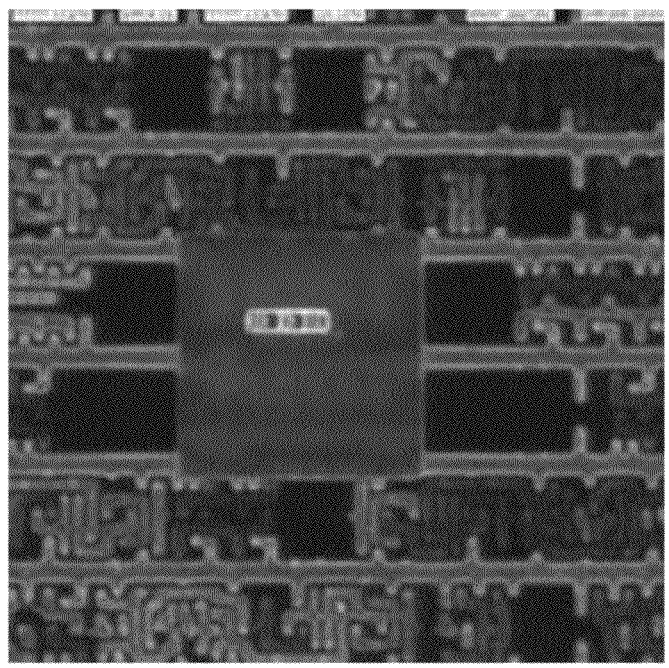
FIG. 5 is an image of the feature in FIG. 4 with a dielectric patch deposited.
Figure 6:
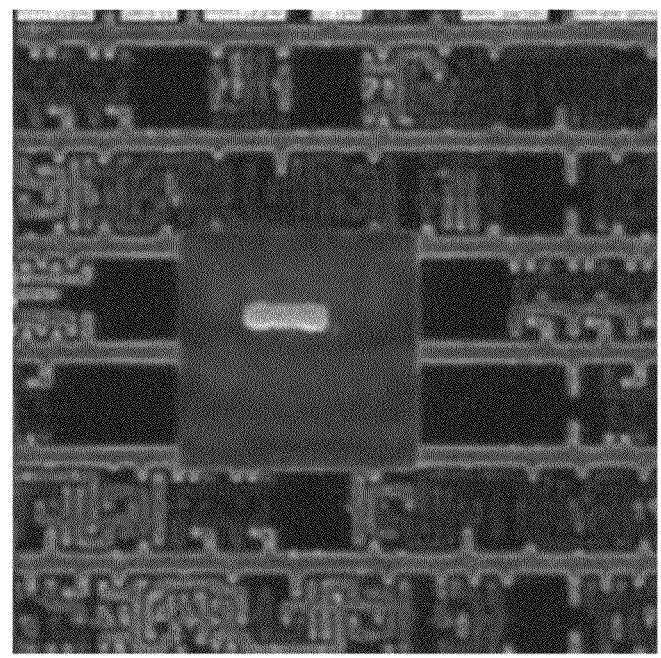
FIG. 6 is an image of the feature in FIG. 4 with the nodes of the known feature and of the unknown feature being shorted.

In FIG. 4, the known feature (a buffer) is biased and the FIB derived image shows the feature in high contrast relative to the other features on the IC. In FIG. 5, a dielectric patch is deposited on the known feature and the nodes of the known feature and an unknown feature (i.e. a non-biased feature) are exposed. In FIG. 6, the nodes of the known feature and of the unknown feature are shorted by depositing conductor material between the two nodes. Once shorted, the two nodes are thus coupled and applying a bias to the shorted nodes has the effect of applying a bias to whatever nodes, features, or components are coupled to the unknown feature. When a focused ion beam is thus applied to the IC while the bias is being applied, these nodes, features, or components coupled to the unknown feature will also appear in high (or higher) contrast when compared to the unbiased parts or areas of the IC.

Figure 7:
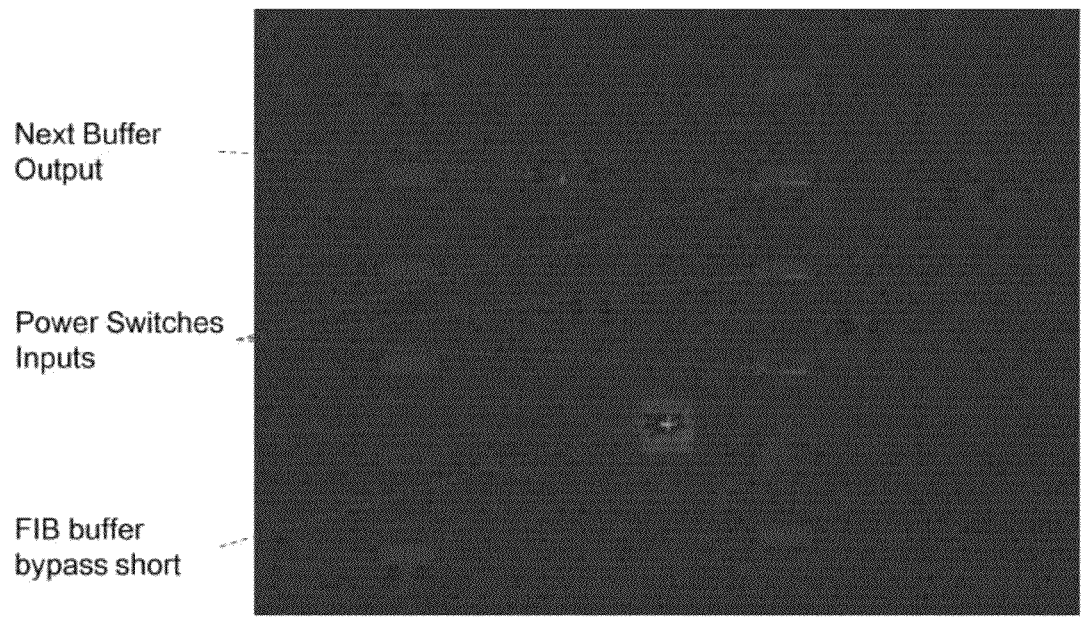
FIG. 7 is an image of the integrated circuit of FIG. 6 showing the different parts of the IC being in high contrast due to the bias being applied to the known feature.

Referring to FIG. 7, the shorted area (i.e. the area to which a bias has been applied) is illustrated in the lower middle part of the image. The features of the IC which are coupled to the unknown feature appear in higher contrast than the rest of the IC. As can be seen in FIG. 7, these features include inputs to the power switches as well as an output for the next buffer.

It should be noted that the example given in FIGS. 3A-7 should not be taken as being limiting to the present invention. Any feature, node, or component on an integrated circuit or microchip can be used as a first or initial component or node. This first component can then be shorted or coupled with a second component by any appropriate means prior to applying a bias and a focused ion beam to the integrated circuit. While the example given uses FIB to deposit and remove dielectric as well as metal interconnect, other techniques may be used. Also, while the example uses a gallium ion source for the focused ion beam, other ion sources, such as elemental gold, iridium, xenon, neon, as well any other suitable ion sources, may be used.

It should also be noted that, for best results, the first and second nodes or components which are to be coupled to each other are preferably not coupled to one another by way of the integrated circuit prior to being coupled to one another for biasing and imaging purposes.

In one implementation, to work one aspect of the invention, an integrated circuit chip or die is first prepared using standard known back-side sample preparation methods. This involves mounting the die to an insulating carrier face-down, then removing the die bulk silicon using wet or dry etching until the gate level components are exposed. The die can be further processed from the back using standard techniques to expose the specific layer of interest. One approach would be to expose the Metal 1 level. Once the level or component of interest has been exposed, a signal path is extended from an external source to the node, component, or feature of interest. A bias voltage is applied to the signal node or feature, typically using an external power supply.

After applying the bias voltage, the sample is then placed inside a focused ion beam chamber. The chamber is then pumped with a vacuum pump, and the sample is exposed to a FIB beam. By varying the beam conditions, the imaging detector conditions, and the external bias voltage, the signal node can be made to show up with very high contrast compared to the rest of the circuitry in the Secondary Electron (SE) imaging detector image. The node or feature of interest can be made to appear illuminated while the rest of the circuitry is dark.

Once the feature of interest has been biased and been made to appear in high contrast, the high contrast area can be extended. Using the ability of the focused ion beam technique to deposit insulating material and conducting material very precisely, the signal path is extended to a new section or feature of circuitry. In the case of a single transistor, the original biasing signal might be applied to one node of a transistor (e.g. a gate, source or drain contact) and, using focused ion beam deposition techniques, the biasing signal can be extended to another node of the transistor (e.g. gate, source or drain contact). Once the bias signal has been extended to the new feature, any other nodes connected to that node will appear illuminated in the SE image.

It should be noted that, while the signal path may extend invisibly through many metal layers (more than 10 on a modern IC), wherever it is connected to another metal 1 area will be instantly visible in the SE image.

Once the new connected node has been revealed, the procedure can be repeated and the next node can thus be illuminated. By continuing to traverse the circuit and form these connections, the circuit can be followed across the IC die. As can be imagined, for circuits involving a number of transistors, this process simply involves the deposition of conductor to short the source contact to the drain contact as well as the application of a bias voltage prior to applying the focused ion beam to the sample.

It should be noted that one aspect of the invention may take the form of simply applying an external bias to a component or node prior to applying a focused ion beam to the integrated circuit. After applying the focused ion beam, an image is taken using an electron detector. The features or components on the integrated circuit which are coupled to the component or node to which the bias was applied will show up in high contrast on the resulting image. The method can be used to identify nodes or components interconnected through a common path on the integrated circuit.

The technique outlined above can be applied to gate level circuitry, contact level circuitry, or any desired metal level (such as Metal 1).

It should be noted that the images obtained using the above outlined process may be further processed to glean further information from the images. As an example, image enhancement techniques may be applied to digital versions of the images derived from the above process to further clarify components, nodes, and features on the IC.

It should further be noted that the images gathered in multiple iterations of the process may be used to determine which features have been highlighted by the application of a bias to relevant part or parts of the integrated circuit. As an example, an image for iteration A (prior to applying a bias to a shorted part of the IC) may be compared to the image for iteration A+1 (subsequent to the application of the bias) to see which parts of the IC have been highlighted. Image subtraction, image manipulation, as well as image addition techniques may be used to automate the process by which the highlighted or highly contrasted parts of the image are determined.

Regarding the conditions and settings for the focused ion beam, various parameters may be adjusted and/or set for optimum resulting image quality. These parameters include voltage, current, dwell time, as well as other parameters. Such parameters and their effects and settings are well known to those versed in the art of focused ion beam techniques. For the electron detector, parameters which may be adjusted to obtain a suitable image quality include, among others, brightness, contrast, and line averaging.

The bias applied to the features of interest may range from +24V+ to −24V. The bias may depend on the focused ion beam conditions as well as the characteristics of the IC being imaged. As examples, the characteristics of the IC may include pattern density, conductor line width/resistance, dielectric quality and conductor quality. Preferably, bias current will be limited to prevent arcing between conductors. The bias current is thus preferably in the microampere range.

Figure 8:
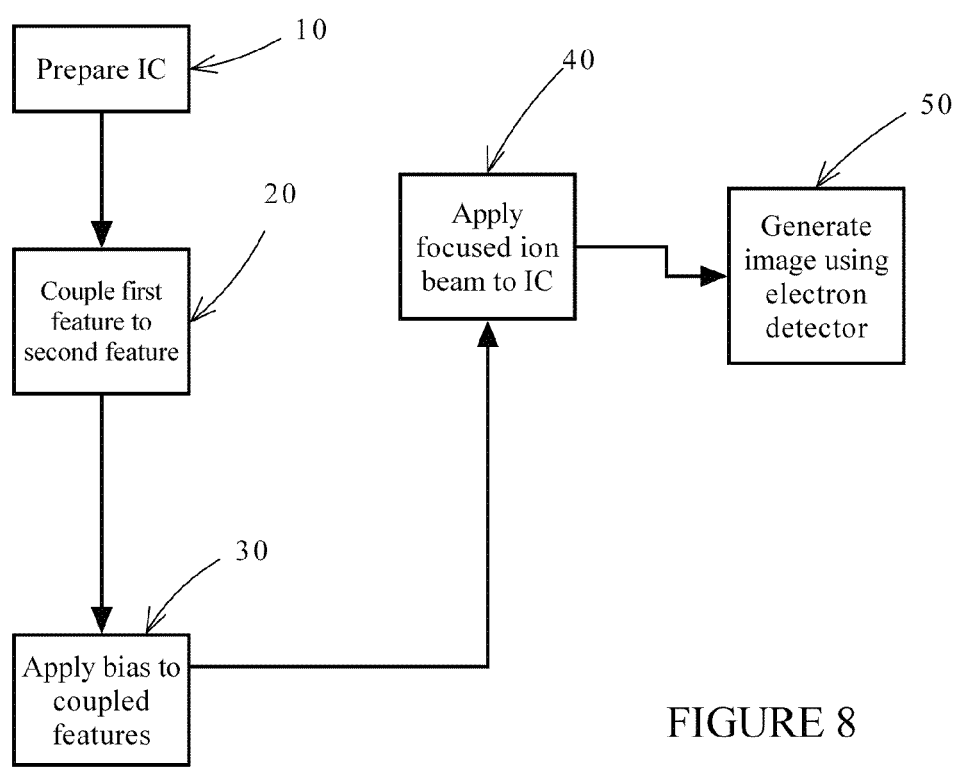
FIG. 8 is a flowchart detailing the steps in a method according to one aspect of the invention.

One aspect of the invention may be seen as a process detailed by the flowchart in FIG. 8. The process begins at step 10, that of preparing the IC. As noted above, this step may involve exposing the components in the IC to the gate level. Step 20 is that of coupling one feature or node to another. This may be done using different techniques including FIB dielectric deposition. Once a known feature has been coupled to an unknown feature (i.e. a feature whose interconnections are not known), a bias can then be applied to the coupled features (step 30). A focused ion beam can now be applied to the IC (step 40). An electron detector can then be used to generate an image of the IC (step 50). The IC features attached to the biased nodes or features will thus be in high contrast in the resulting image.

A person understanding this invention may now conceive of alternative structures and embodiments or variations of the above all of which are intended to fall within the scope of the invention as defined in the claims that follow.

We claim:

1. A method for imaging circuitry on an integrated circuit, the method comprising:
    a) applying an external electrical bias on to a first portion of said integrated circuit;
    b) exposing said integrated circuit to a focused ion beam;
    c) gathering an image of said integrated circuit;
wherein said image gathered in step c) shows a second portion of said integrated circuit which is in high contrast compared to a rest of said image, said first and second portions being interconnected through a common path in said integrated circuit.

2. A method for imaging circuitry on an integrated circuit, the method comprising:
    a) coupling a first part of said integrated circuit with a second part of said integrated circuit;
    b) applying a bias voltage to said first part;
    c) exposing said integrated circuit to a focused ion beam; and
    d) gathering an image of said integrated circuit using an electron detector;
wherein said first part and said second part are not coupled through said integrated circuit; and
wherein said image gathered in step d) has at least one portion in high contrast compared to a rest of said image, said at least one portion being a portion of said integrated circuit which is coupled to said second part of said integrated circuit.

3. A method according to claim 2 wherein steps a) to d) are repeated using said at least one portion as said second part and an integrated circuit feature normally unconnected to said at least one portion as said first part.

4. A method according to claim 3 wherein multiple iterations of said method are performed and further including a step of comparing images of said integrated circuit gathered at during said multiple iterations to trace which integrated circuitry features are coupled to one another.

5. A method according to claim 2 wherein step a) is accomplished by depositing dielectric material and metal interconnect material between said first part and said second part.

6. A method according to claim 2 wherein said focused ion beam is derived from a gallium ion source.

7. A method for tracing interconnections in an integrated circuit, the method comprising:
   a) removing layers of said integrated circuit to expose components of said integrated circuit;
   b) coupling a first node of said integrated circuit to a second node of said integrated circuit;
   c) applying an external bias voltage to said first node;
   d) capturing an image of at least a portion of said integrated circuit using a focused ion beam and an electron detector;
   e) determining which components of said integrated circuit are illustrated in high contrast in said image;
wherein, prior to step b), said first node and second node are not coupled to one another through said integrated circuit.

8. A method according to claim 7 further including the step of repeating steps b) to e) using at least one of said components illustrated in said image as said second node and a node unconnected to said components through said integrated circuit as said first node.

9. A method according to claim 7 wherein said focused ion beam is derived from a gallium ion source.

10. A method according to claim 7 wherein said first node and said second node are nodes on a transistor.

11. A method according to claim 7 wherein steps b) to e) are repeated multiple times using different nodes on said integrated circuit and including a step of comparing images captured using said steps to determine which nodes are connected to which components on said integrated circuit.

12. A method according to claim 7 wherein step b) is accomplished by shorting said first node and said second node using material external to said integrated circuit.

13. A method according to claim 12 wherein said step b) is accomplished by depositing dielectric material and metal interconnect material between said first node and said second node.

14. A method according to claim 7 further including a step of applying image enhancement techniques to a digital version of said image to enhance said image.

15. A method according to claim 7 further including the step of iteratively repeating steps b) to e) using at least one component illustrated in an image from a previous iteration as said second node and a node unconnected to said component through said integrated circuit as said first node.

* * * * *